(12) United States Patent
Sägmüller et al.

(10) Patent No.: US 7,907,259 B2
(45) Date of Patent: Mar. 15, 2011

(54) LASER MICRODISSECTION METHOD, CONTROL SYSTEM FOR A LASER MICRODISSECTION DEVICE AND CARRIER DEVICE

(75) Inventors: Bernd Sägmüller, Laudenbach (DE); Renate Burgemeister, Ismaning (DE); Yilmaz Niyaz, Augsburg (DE)

(73) Assignee: Carl Zeiss MicroImaging GmbH (DE)

( * ) Notice: Subject to any disclaimer, the term of this patent is extended or adjusted under 35 U.S.C. 154(b) by 363 days.

(21) Appl. No.: 12/144,144

(22) Filed: Jun. 23, 2008

(65) Prior Publication Data
US 2009/0002682 A1 Jan. 1, 2009

Related U.S. Application Data

(63) Continuation of application No. PCT/EP2006/010912, filed on Nov. 14, 2006.

(30) Foreign Application Priority Data

Dec. 22, 2005 (DE) .......... 10 2005 061 561

(51) Int. Cl.
*G01N 1/00* (2006.01)
(52) U.S. Cl. ...................... 356/36; 435/40.52
(58) Field of Classification Search .......... 356/36; 435/30, 40.52
See application file for complete search history.

(56) References Cited

U.S. PATENT DOCUMENTS

| 5,356,751 | A | 10/1994 | Cairncross et al. | |
| 7,189,526 | B2* | 3/2007 | Kojima et al. | 435/30 |
| 2004/0185522 | A1 | 9/2004 | Ogawa et al. | |

FOREIGN PATENT DOCUMENTS

| DE | 695 10 925 T2 | 2/2000 |
| DE | 100 03 588 A1 | 8/2001 |
| DE | 101 09 259 A1 | 9/2001 |
| DE | 10 2004 051 508 A1 | 6/2005 |
| DE | 10 2004 023 262 A1 | 12/2005 |
| EP | 0 926 480 A2 | 6/1999 |
| WO | 97 13838 | 4/1997 |
| WO | 97 29355 A1 | 8/1997 |
| WO | 98 362961 A1 | 8/1998 |
| WO | 01 73398 A1 | 10/2001 |
| WO | 02 10751 A2 | 2/2002 |
| WO | 02 14833 A1 | 2/2002 |
| WO | 2004 019007 A1 | 3/2004 |
| WO | 2005 051718 A1 | 6/2005 |
| WO | 2005 106423 A1 | 11/2005 |

OTHER PUBLICATIONS

"High-quality RNA preparation for transcript profiling of osteocytes from native human bone microdissections", Eisenberger et al., Analytical Biochemistry, Academic Press, vol. 335, No. 2, Dec. 15, 2004.
"Laser Capture Microdissection", Emmert-Buck et al., American Association for the Advancement of Science, vol. No. 274, No. 5289, Nov. 8, 1996.

* cited by examiner

Primary Examiner — L. G Lauchman
(74) Attorney, Agent, or Firm — Mayback & Hoffman PA.; Gregory L. Mayback; Rebecca A. Tie (57) ABSTRACT

A microdissection method for separating and taking a target zone of a biological preparation, disposed on a carrier device with a laser light-absorbent incisable layer and a carrier means, comprises cutting the preparation and the incisable layer along an edge segment of the target zone and removing of a non-excised segment of the incisable layer from the carrier means.

15 Claims, 6 Drawing Sheets

LASER MICRODISSECTION METHOD, CONTROL SYSTEM FOR A LASER MICRODISSECTION DEVICE AND CARRIER DEVICE

CROSS-REFERENCE TO RELATED APPLICATION

This is a continuing application, under 35 U.S.C. §120, of copending international application No. PCT/EP2006/010912, filed Nov. 14, 2006, which designated the United States and was not published in English; this application also claims the priority, under 35 U.S.C. §119, of German patent application No. DE 10 2005 061 561.9, filed Dec. 22, 2005; the prior applications are herewith incorporated by reference in their entirety.

BACKGROUND OF THE INVENTION

Field of the Invention

The present invention relates to a laser microdissection method for separating and obtaining objects from a preparation, in particular, a biological preparation, as well as to a control system for a laser microdissection device and to a carrier device for receiving the preparation. In particular, the present invention relates to a laser microdissection method and laser microdissection system for obtaining small, medium, and large microdissectate quantities.

A conventional laser microdissection system in the name of the Applicant is known, for example, from International Publication Nos. WO 97/29355 A or WO 01/73398 A. This laser microdissection system allows computer-assisted selection of individual biological or non-biological objects that are disposed on a planar carrier to be performed, and it allows them to be processed by a laser beam. In particular, the objects can be transported to one or more collection devices by being processed with the laser beam. A plurality of transport processes are possible, induced directly or indirectly by the laser beam, and these are described in the cited documents. For example, a selected object may be fully or partially separated from the surrounding preparation by the laser beam, and thus released. The released object may then be accelerated or "catapulted" from the carrier to a collection device by a laser-induced transport process with the aid of a laser pulse, which is directed onto the object. If the object is not fully released, but instead is still connected to the surrounding preparation by a residual web, then the laser pulse may be used both for cutting through the residual web and for catapulting the object to the collection device.

In principle, the laser-induced transport process may be carried out even without the respectively selected object being released beforehand, if the laser energy and/or the size of the laser focus on the preparation is or are selected so that the force acting on the object is sufficient both for detaching the object from the preparation and also for accelerating it to the collection device.

Laser microdissection systems make it possible to separate and take, as well as to sort and obtain, both biological and non-biological objects. In particular, laser microdissection allows contactless separation of biological objects, for example, individual cells, from a preparation. Because the biological objects are not damaged or compromised by the separating and/or catapulting process, after having been separated and taken, they are available for further studies. For example, tumor cells may be separated from healthy cells of a tissue section and may be taken and subsequently studied.

Conventional laser microdissection systems and methods, however, have the disadvantage that it is often difficult to separate and take a sizeable quantity of material of a preparation. While it is possible to separate and take a greater number of objects from the preparation by scanning a larger area of the preparation, nevertheless, scanning the larger area and separating and taking the greater number of objects often requires a long time. Furthermore, the possibility of separating and taking a greater number of objects is often also restricted by the collecting capacity of the collection device. If the total mass or total volume of objects to be transported to the collection device is too large, then the transported objects may possibly no longer be held in the collection device and may be lost.

Therefore, there is a need in the art for an improved laser microdissection method and an improved laser microdissection system. In particular, there is a need in the art for a laser microdissection method and a laser microdissection system that make it possible to separate and take even a sizeable number of objects from the preparation, i.e., a larger segment of the preparation.

According to one embodiment of the invention, a microdissection method is provided. The microdissection method comprises providing a carrier device having a laser light-absorbent incisable layer and a carrier for carrying the laser light-absorbent incisable layer, applying a preparation on the incisable layer, in particular, a biological preparation, selecting a target zone to be separated of the preparation, cutting the preparation and the incisable layer along an edge segment of the target zone by laser irradiation to subdivide the incisable layer into at least one excised segment and into a non-excised segment, and removing the non-excised segment of the incisable layer from the carrier. The target zone of the preparation corresponds to the totality of objects to be separated, which may define a single spatially connected region or a plurality of respectively spatially connected regions.

According to another embodiment of the invention, a control system for a microdissection system is provided. The control system for the laser microdissection system (the latter comprising a structure for holding a carrier device for a preparation and a laser light source for generating a laser beam to be directed onto the preparation to cut the preparation) comprises a controller adapted to control the holding structure and the laser light source so that the preparation is cut along at least one incision line, and an evaluator adapted to generate an evaluation signal based upon geometrical properties of the target zone to be separated.

According to another embodiment of the invention, a carrier device is provided. The carrier device comprises a carrier and a laser light-absorbent incisable layer, the incisable layer being applied on the carrier so that it is removable from the carrier in a direction having a vertical component, i.e., it can be removed or rolled off vertically or at an oblique angle.

With the foregoing and other objects in view, there is provided, in accordance with the invention, a method for performing microdissection, including the steps of providing a carrier device with a laser light-absorbent incisable layer and a carrier for carrying the laser light-absorbent incisable layer, applying a preparation on the incisable layer, selecting a target zone to be separated from the preparation, cutting the preparation and the incisable layer along an edge segment of the target zone by laser irradiation to subdivide the incisable layer into at least one excised segment and a non-excised segment, and removing the non-excised segment of the incisable layer from the carrier.

In accordance with another mode of the invention, the cutting step is carried out to excise the target zone and the non-excised segment of the incisable layer is removed while the target zone remains on the carrier.

In accordance with a further mode of the invention, the incisable layer is applied displaceably on the carrier and the target zone us centrifuged off together with the at least one excised segment of the incisable layer from the carrier for further processing of the target zone.

In accordance with an added mode of the invention, the cutting step is carried out to excise a preparation segment not containing the target zone and the target zone is removed from the carrier together with the non-excised segment of the incisable layer when the non-excised segment is removed.

In accordance with an additional mode of the invention, the removing step is carried out manually.

In accordance with yet another mode of the invention, the carrier comprises a first incisable layer support and a second support operable to support the first support and there is provided the step of configuring the carrier device to dispose the first support substantially between the second support and the incisable layer.

In accordance with yet a further mode of the invention, the first support is removed from the second support after the non-excised segment of the incisable layer is removed from the carrier.

In accordance with yet an added mode of the invention, the first support is manually removed from the second support.

In accordance with yet an additional mode of the invention, an overview image of the preparation is generated and the target zone selecting step is carried out in a user-defined fashion or at least partially automatically based upon the overview image.

In accordance with again another mode of the invention, the carrier is at least partially transparent and there is provided the step of irradiating a laser beam onto the carrier device on the same side as the carrier to cut the preparation and the incisable layer.

In accordance with again a further mode of the invention, a laser beam is irradiated onto the carrier device on the same side as the incisable layer to cut the preparation and the incisable layer.

In accordance with again an added mode of the invention, the target zone is a plurality of respectively geometrically connected target zone regions having edge segments, and there is provided the step of cutting the preparation and the incisable layer by laser irradiation along an edge segment of each of the target zone regions before the non-excised segment of the incisable layer is removed.

In accordance with again an additional mode of the invention, the target zone is analyzed by molecular genetics after the non-excised segment of the incisable layer is removed from the carrier.

In accordance with still another mode of the invention, the preparation is a biological preparation.

With the objects of the invention in view, there is also provided a method for performing microdissection, including the steps of providing a carrier device with a laser light-absorbent incisable layer and a means for carrying the laser light-absorbent incisable layer, applying a biological preparation on the incisable layer, selecting a target zone to be separated from the preparation, cutting the preparation and the incisable layer along an edge segment of the target zone by laser irradiation to subdivide the incisable layer into at least one excised segment and into a non-excised segment, and removing the non-excised segment of the incisable layer from the carrier means.

With the objects of the invention in view, there is also provided a laser microdissection control system for processing a preparation applied on a carrier device, the laser microdissection system including a carrier device holder, a laser light source operable to generate a laser beam to be directed onto the preparation and cut the preparation, and a control system including a controller operable to control at least one of the carrier device holder and the laser light source to induce a relative movement between the carrier device and the laser beam to cut the preparation along at least one incision line, a target zone evaluator for evaluating a selected target zone to be separated, the evaluator operable to generate an evaluation signal dependent upon a geometrical property of the target zone, and the controller operable to determine the at least one incision line dependent upon the evaluation signal and the selected target zone.

In accordance with still a further feature of the invention, the evaluator is operable to generate the evaluation signal assume first and second values and the controller is operable to determine the at least one incision line in response to the evaluation signal having the first value so that a preparation segment not containing the target zone is excised.

In accordance with still an added feature of the invention, the controller is operable to determine the at least one incision line in response to the evaluation signal having the second value so that the target zone is excised.

In accordance with still an additional feature of the invention, the evaluator is operable to generate the first value of the evaluation signal if the target zone is a connected region and, otherwise, to generate the second value of the evaluation signal.

In accordance with another feature of the invention, the evaluator is operable to generate the first value of the evaluation signal if an area of the target zone relative to an area of the preparation exceeds a predetermined threshold value and, otherwise, to generate the second value of the evaluation signal.

With the objects of the invention in view, there is also provided a laser microdissection control system for processing a biological preparation applied on a carrier device, the laser microdissection system including means for holding the carrier device, a laser light source operable to generate a laser beam to be directed onto the preparation and cut the preparation, and a control system including means for controlling at least one of the holding means and the laser light source to induce a relative movement between the carrier device and the laser beam to cut the preparation along at least one incision line, means for evaluating a selected target zone to be separated and operable to generate an evaluation signal dependent upon a geometrical property of the target zone, and the control means operable to determine the at least one incision line dependent upon the evaluation signal and the selected target zone.

With the objects of the invention in view, there is also provided a microdissection system, including a laser microdissection control system operable to process a biological preparation applied on a carrier device and a laser microdissection system including a carrier device holder, a laser light source operable to generate a laser beam to be directed onto the preparation to cut the preparation, a control system including a controller operable to control at least one of the carrier device holder and the laser light source to induce a relative movement between the carrier device and the laser beam to cut the preparation along at least one incision line, a target zone evaluator for evaluating a selected target zone to be separated, the evaluator operable to generate an evaluation signal dependent upon a geometrical property of the target zone, and the controller operable to determine the at least one incision line dependent upon the evaluation signal and the selected target zone.

With the objects of the invention in view, there is also provided a biological preparation carrier device for separating a target zone of the preparation by laser irradiation, including a laser light-absorbent incisable layer for receiving the preparation and a carrier for carrying the incisable layer and having the incisable layer removably applied thereon.

In accordance with a further feature of the invention, there is provided a layer of a lubricant between the incisable layer and the carrier, the layer facilitating displacement of the incisable layer relative to the carrier when a force is exerted parallel to a plane defined by the incisable layer. In an embodiment, the lubricant is glycerol.

In accordance with an added feature of the invention, the incisable layer is a membrane comprising a material and/or made of the material, and the material is any of polyethylene naphthalate (PEN), polyethylene terephthalate (PET) or polyester (POL).

In accordance with an additional feature of the invention, the carrier includes a first incisable layer support and a second support operable to support the first support, the first support being applied removably on the second support, and the first support is disposed substantially between the second support and the incisable layer.

In accordance with yet another feature of the invention, there is provided a layer of a lubricant disposed between the first and second supports, the layer facilitating displacement of the first support relative to the second support when a force is exerted parallel to a plane defined by the first support.

In accordance with yet a further feature of the invention, there is provided an appendage on the incisable layer at least partially protruding laterally beyond the first support.

In accordance with yet an added feature of the invention, the carrier comprises a first incisable layer support and a second support operable to support the first support, the first support being applied removably on the second support, the first support is disposed substantially between the second support and the incisable layer, and a further layer of a further lubricant between the first and second supports, the further layer facilitating displacement of the first support relative to the second support when a force is exerted parallel to a plane defined by the first support.

In accordance with a concomitant feature of the invention, the further lubricant is glycerol, the first support is a membrane of polytetrafluoroethylene (PTFE), the second support is a membrane of polytetrafluoroethylene (PTFE) or a glass plate, and the incisable layer has an appendage at least partially protruding laterally beyond the first support.

Although the invention is illustrated and described herein as embodied in a laser microdissection method for separating and obtaining objects from a preparation, a control system for a laser microdissection device, and a carrier device, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an", as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically.

As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure.

Preferred exemplary embodiments of the invention will be explained below with reference to the drawings.

DETAILED DESCRIPTION OF THE INVENTION

A microdissection method according to one embodiment of the invention includes the steps of providing a carrier device with a laser light-absorbent incisable layer and a carrier for carrying the laser light-absorbent incisable layer. A preparation is applied on the incisable layer, in particular, a biological preparation. A target zone to be separated from the preparation is selected, the preparation and the incisable layer is cut along an edge segment of the target zone by laser irradiation to subdivide the incisable layer into at least one excised segment and into a non-excised segment. The non-excised segment of the incisable layer is removed from the carrier. The target zone of the preparation corresponds to the totality of objects to be separated, which may define a single spatially connected region or a plurality of respectively spatially connected regions. The incisable layer may be an incisable membrane or a vapor-deposited or sputtered layer, for example, a metal layer or a polyalcohol applied using an immersion bath. Because the target zone is separated and taken by cutting with laser irradiation and subsequent removal of the non-excised segment of the incisable layer, while it is possible to transport objects from the preparation to a collection device in a laser-induced fashion according to the method, this is no longer absolutely necessary. It is possible to separate and take small, medium, and large microdissectate quantities.

The cutting of the preparation and the incisable layer may be carried out to excise the target zone and the segments of the incisable layer disposed therebelow or thereabove. In this case, the target zone is disposed on the excised segment or the excised segments of the incisable layer and, when the non-excised segment of the incisable layer is removed from the carrier, it remains together with the excised segment or the excised segments of the incisable layer on the carrier. Such a configuration of the method is advantageous, in particular, when the target zone has a plurality of mutually separated regions or occupies an area that is small compared with the area of the zones of the preparation that do not belong to the target zone. The segments of the preparation that remain on the carrier, i.e., the target zone, may be centrifuged off from the carrier for further processing. To this end, the carrier together with the excised segments of the incisable layer, which are disposed thereon, and the target zone of the preparation are preferably rolled up, put into a centrifuge tube, and then centrifuged. An incisable layer, for example, an incisable membrane or another layer that dissolves in the target vessel, may furthermore be used in this case.

Cutting of the preparation and the incisable layer may also be carried out to excise preparation segments not belonging to the target zone, together with segments of the incisable layer that are disposed below or above these segments. In such a case, the target zone is disposed on the non-excised segment of the incisable layer and is removed together with it from the carrier. Such a configuration of the method is advantageous in particular when the target zone comprises a single connected region, which may also spatially surround one or more islands of segments of the preparation that do not belong to the target zone. Because the preparation segments not belonging to the target zone remain on the carrier when the non-excised segment of the incisable layer is removed, the target zone will also be successfully separated and taken in this case.

Irrespective of whether the target zone or the preparation segments not belonging to the target zone is or are excised, the removal of the non-excised segment of the incisable layer may, in particular, be carried out by manually removing the non-excised segment of the incisable layer from the carrier. The removal may also be carried out using a machine. By the removal, the target zone is mechanically isolated from the preparation segments not belonging to the target zone. Because the non-excised segment of the incisable layer can be removed as a whole, this method step can be carried out comparatively quickly.

The carrier may comprise a first support and a second support, the carrier device being configured so that the first support is disposed substantially between the second support and the incisable layer. The method may then comprise the further step of removing the first support from the second support. Because, with this configuration of the carrier device, the excised segment or the excised segments of the incisable layer together with the corresponding excised segments of the preparation remain on the first support after removal of the incisable layer, the excised segment or the excised segments of the preparation may be delivered more simply for further processing or analysis by removing the first support from the second support.

A laser beam used to cut the preparation and the incisable layer may be irradiated onto the carrier device both on the same side as the incisable layer and on the same side as the carrier. In the latter case, however, the carrier must be transparent at least in the spectral range of the laser beam. The method according to various embodiments of the invention may, therefore, be used both in an erect microscope and in an inverse microscope so that it can be carried out in a wide variety of systems.

Irrespective of whether the target zone is removed with the non-excised segment of the incisable layer or remains on the carrier, the target zone of the preparation, i.e., the objects of the preparation that are contained therein, may be processed further in a wide variety of ways. As already mentioned above, the target zone may be centrifuged off. Furthermore, for example, an impression of the target zone may be eluted by a digestion gel of solid-phase extraction, or process chemicals may be applied directly onto the target zone, on the carrier or on the non-excised segment of the incisable layer. The tissue of the objects of the preparation that are contained in the target zone may then, for example, be lysed and further analyzed, for example, by nanoliquid chromatography or by mass-spectroscopy methods.

By the method according to embodiments of the invention, either the target zone of the preparation is excised by laser irradiation or the preparation segments not contained in the target zone are excised by laser irradiation; the decision about whether the target zone or the segments not contained in the target zone is or are to be excised may be taken in a user-defined fashion or automatically by a control system of a laser microdissection system.

A control system according to one embodiment of the invention for a laser microdissection system, the latter comprising a structure for holding a carrier device for a preparation and a laser light source for generating a laser beam to be directed onto the preparation to cut the preparation, comprises a controller adapted to control the structure and the laser light source so that the preparation is cut along at least one incision line, and an evaluator that are adapted to generate an evaluation signal based upon geometrical properties of the target zone to be separated. The evaluation signal may, in particular, be such that it can assume a first value and a second value. The controller determines the at least one incision line so that, depending on the value of the evaluation signal, either the target zone of the preparation or a preparation segment not contained in the target zone is excised. At least semi-automated implementation of the method according to embodiments of the invention can, thus, be carried out.

In particular, the evaluator may be adapted so that they generate the evaluation signal having the first or second value according to one of the criteria mentioned above. For example, the evaluator may be adapted to generate the evaluation signal with the first value if the target zone is a connected region and/or the area of the target zone relative to a total area of the preparation exceeds a particular threshold value so that a segment not contained in the target zone or a plurality of the preparation segments not contained in the target zone is or are excised. The determination of incision lines according to predetermined criteria can, thus, be substantially automated.

The evaluator may be integral with the controller.

A carrier device according to one embodiment of the invention comprises a carrier and a laser light-absorbent incisable layer, the incisable layer being applied on the carrier so that it is removable from the carrier in a direction with a vertical component, i.e., it can be removed or rolled off vertically or at an oblique angle. Only the incisable layer is cut when a laser beam is illuminated in so that, when using the carrier device according to an embodiment of the invention, particular regions of the incisable layer are excised but the carrier is not cut. In particular, the carrier device is configured so that a non-excised segment of the incisable layer can be removed from the carrier after the excision of one or more segments of the incisable layer, while the excised segment or the excised segments of the incisable layer remain on the carrier. Such a carrier device may be used in the microdissection method according to embodiments of the invention and, thus, makes it possible to separate and take small, medium, and large quantities of objects from the preparation.

In a preferred embodiment, a layer of a lubricant, for example, glycerol, is provided between the incisable layer and the carrier. In other exemplary embodiments, a layer of a polyalcohol or a mixture of a plurality of polyalcohols is provided between the incisable layer and the carrier. Such a layer may serve several purposes. For example, it may make it easier to centrifuge the excised segment or the excised segments of the incisable layer off from the carrier and/or to remove the non-excised segment of the incisable layer from the carrier. It may also serve the purpose of holding the excised segment or the excised segments of the incisable layer on the carrier, when the non-excised segment of the incisable layer is removed therefrom.

In another exemplary embodiment, the incisable layer touches the carrier directly, and the incisable layer and the carrier are held together by adhesion forces.

In a preferred exemplary embodiment, the incisable layer may comprise a material, or be made from a material, which is selected from the group consisting of polyethylene naphthalate (PEN), polyethylene terephthalate (PET) or polyester (POL). The incisable layer may have a thickness of, for example, 1.25 μm.

In particular, the carrier may, in turn, have a double or multiple layer structure. The carrier may, in particular, comprise a first support and a second support, the carrier device being configured so that the first support is disposed substantially between the second support and the incisable layer. The first support is preferably applied on the second support so that it can be removed therefrom. Such a configuration of the carrier may facilitate further processing of excised segments of the preparation because the first support, on which the excised segments of the preparation are disposed together with the excised segments of the incisable layer, can be removed from the second support. A layer of glycerol or a layer of a polyalcohol may, in turn, be provided between the first support and the second support.

The first and/or the second support may be a membrane or film made from polytetrafluoroethylene (PTFE). The second support may also be a glass plate, for example, a microscope slide. In the latter case, the carrier device may comprise a double-layer membrane, formed from the incisable layer and the first support, as well as the glass plate on which the double-layer membrane is applied by adhesion or by an interposed glycerol layer or a suitable adhesive.

An appendage may be provided on the incisable layer to facilitate removal of the incisable layer from the support. This appendage may protrude laterally beyond an edge of the carrier or be made from a material that does not adhere to the carrier. This will ensure that the appendage easily can be gripped manually and the incisable layer can be removed from the carrier. Similarly, if the carrier comprises a first support and a second support, an appendage may be provided on the first support to facilitate removal of the first support from the second support.

The incisable layer and the carrier are not necessarily joined together by an interposed glycerol layer. Rather, the incisable layer and the carrier may also be held together by adhesion or by an adhesive introduced between them. In the latter case, however, it is necessary to ensure that the incisable layer can still be removed from the carrier.

The microdissection method according to embodiments of the invention, the control system according to embodiments of the invention, and the carrier device according to embodiments of the invention may be used to separate and take small, medium, and large microdissectate quantities for biological studies. In particular, the microdissection method, the control system, and the carrier device according to the various embodiments of the invention may be used to obtain sizeable quantities of a substrate from the preparation in a comparatively short time in order to use them for further studies, for example, in proteomics or other fields of molecular genetics. The method according to embodiments of the invention may be employed both for fixed and fresh tissue and for living tissue.

Figure 1A:
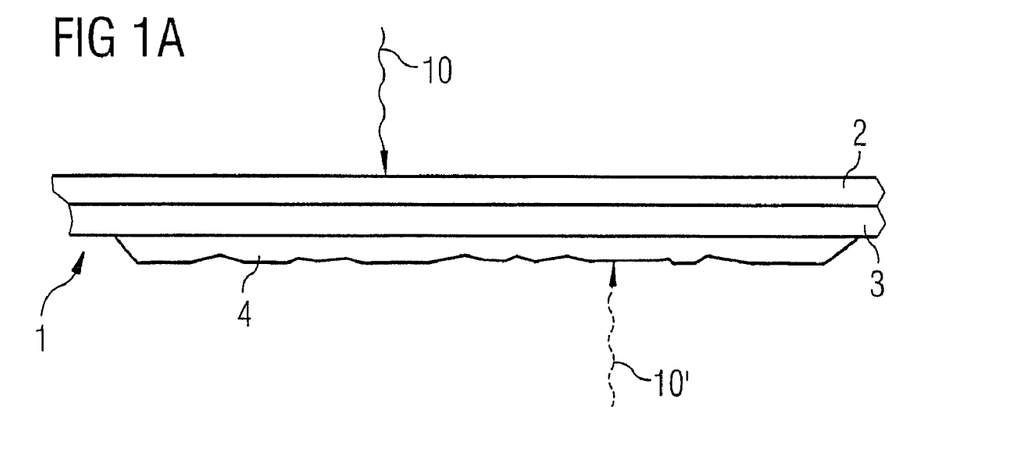
FIGS. 1A and 1B are fragmentary cross-sectional views of the basic principle of a microdissection method according to an exemplary embodiment of the invention, FIG. 1A showing a state before removal of an incisable layer from a carrier and FIG. 1B showing a state after removal of an incisable layer from the carrier.
Figure 1B:
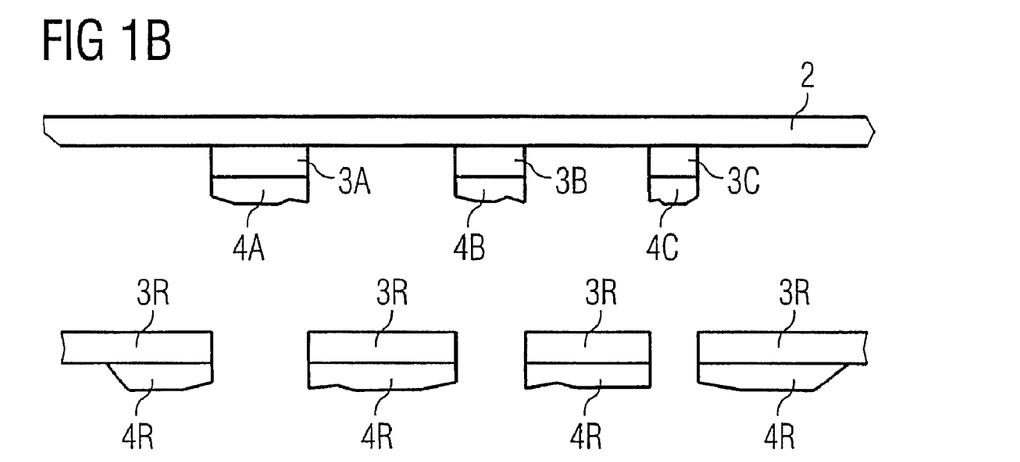

The principle of the microdissection method according to one embodiment the invention will be explained with reference to FIG. 1. FIG. 1 shows a carrier device 1, which includes a carrier 2 and a laser light-absorbent incisable membrane 3. The incisable membrane 3 absorbs the light of a laser beam 10 or 10' irradiated onto the carrier device 1, so that it can be cut by laser irradiation. The incisable membrane 3 may, for example, be made from polyethylene naphthalate (PEN), polyethylene terephthalate (PET) or polyester (POL) and have a thickness in the range of a few micrometers, for example, 1.25 μm.

The carrier 2 may, for example, be a glass plate or a membrane made of polyethylene terephthalates (PTFE). The carrier 2 is, preferably, transparent at least in a spectral range of the laser beam 10, 10'. In this case, the laser beam 10, 10' may be irradiated onto the carrier device 1 on the same side as the carrier 2, like the laser beam 10, or onto the same side as the incisable membrane, like the laser beam 10'. If it is intended that the laser beam 10, 10' can be illuminated in on the same side as the carrier 2, then the carrier 2 is transparent.

A biological preparation 4 is applied on the incisable membrane 3. To separate a particular quantity of desired objects from the preparation 4, for example, cells of a predetermined cell type, a target zone of the preparation is selected that contains the desired objects. The selection of the target zone may, in particular, be carried out in a user-defined fashion or partially or fully automatically. As a function of the selected target zone, a computer induces a position change of the carrier device 1 with the biological preparation 4 relative to the laser beam 10, 10' so that the preparation 4 and the incisable membrane 3 are cut along one or more incision lines, which are determined by the computer.

In this way, segments 3A-C are excised from the incisable membrane 3 so that the incisable membrane 3 is subdivided into the excised segments 3A-C and a non-excised segment 3R. Correspondingly, segments 4A-C are excised from the preparation 4 so that the preparation is subdivided into excised segments 4A-C and a non-excised segment 4R. Each of the excised segments 4A-C of the preparation is disposed on the corresponding excised segment 3A-C of the incisable membrane.

As shown in FIG. 1B, after cutting the preparation and the incisable membrane, the non-excised segment 3R is removed from the carrier 2 together with the non-excised segment 4R of the preparation disposed on the non-excised segment 3R. In particular, the non-excised segment 3R of the incisable membrane 3 may also be removed manually. When the non-excised segment 3R of the incisable membrane 3 is removed from the carrier 2, the non-excised segment 4R of the preparation remains on the non-excised segment 3R of the incisable membrane 3, whereas the excised segments 4A-C of the preparation remain on the carrier 2 together with the excised segments 3A-C of the incisable membrane 3. Both the non-excised segment 4R of the preparation 4 and the excised segments 4A-C of the preparation 4 may be subjected to further processing or analysis, as will be explained in more detail below.

As will now be explained with reference to FIGS. 2A, 2B, 3A, and 3B, in principle, two options are available for separating and taking the target zone, which comprises the biological material of interest, from the rest of the preparation. Specifically, either the target zone itself may be excised so that it remains on the carrier 2 after removing the non-excised segment 3R of the incisable membrane, or preparation segments not contained in the target zone may be excised so that the target zone is removed from the carrier 2 together with the non-excised segment 3R of the incisable membrane 3.

Figure 2A:
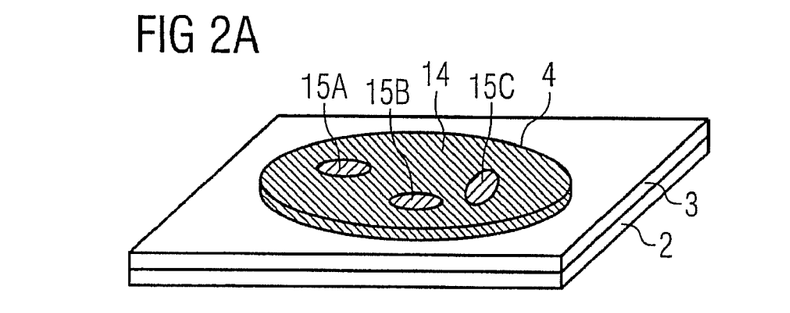
FIGS. 2A and 2B are perspective views of a microdissection method according to a variant of the exemplary embodiment shown in FIGS. 1A and 1B, FIG. 2A showing a state before removal of the incisable layer from the carrier and FIG. 2B showing a state after removal of the incisable layer from the carrier.
Figure 2B:
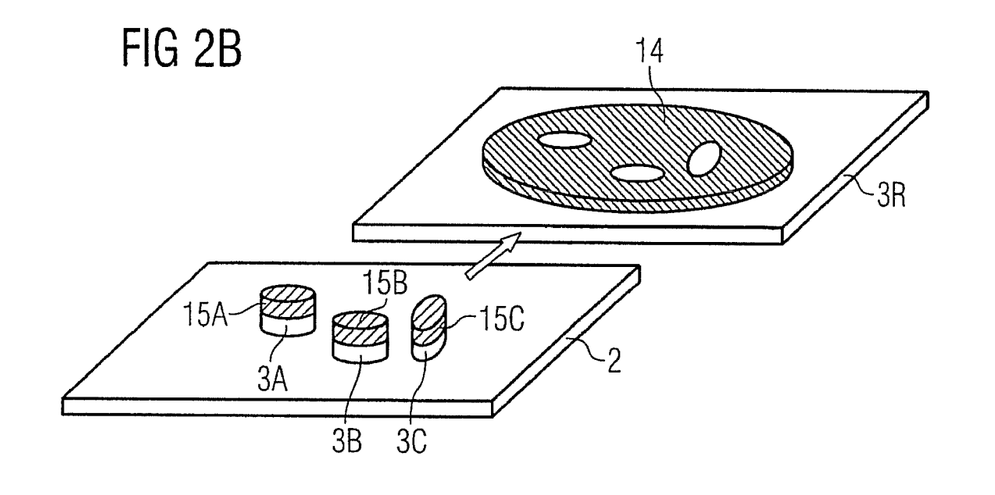

The latter case is represented in FIGS. 2A and 2B. In the example represented, the target zone 14 is a connected region, within which a plurality of islands 15A-C of preparation objects not belonging to the target zone 14 to be separated are disposed. In this case, the microdissection method is preferably carried out so that it is not the target zone itself, but, instead, the islands 15A-C of objects not belonging to the target zone 14 that are excised. When removing the non-excised segment 3R of the incisable membrane 3, as schematically represented by an arrow in FIG. 2B, the target zone 14 is removed together with the non-excised segment 3R of the incisable membrane and is available for further analysis. The undesired objects 15A-C, on the other hand, remain on the carrier 2.

It should be noted that in the exemplary embodiment of the invention as represented in FIGS. 2A and 2B, the preparation 4 and the incisable membrane 3 are cut, not along the entire edge of the target zone 14, but only along the segment of the edge of the target zone 14 that encloses the islands 15A-C.

Figure 3A:
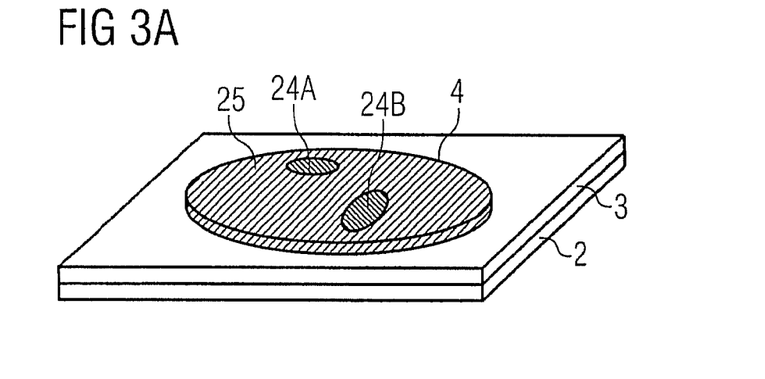
FIGS. 3A and 3B are perspective views of a microdissection method according to another variant of the exemplary embodiment shown in FIGS. 1A and 1B, FIG. 3A showing a state before removal of the incisable layer from the carrier and FIG. 3B showing a state after removal of the incisable layer from the carrier.
Figure 3B:
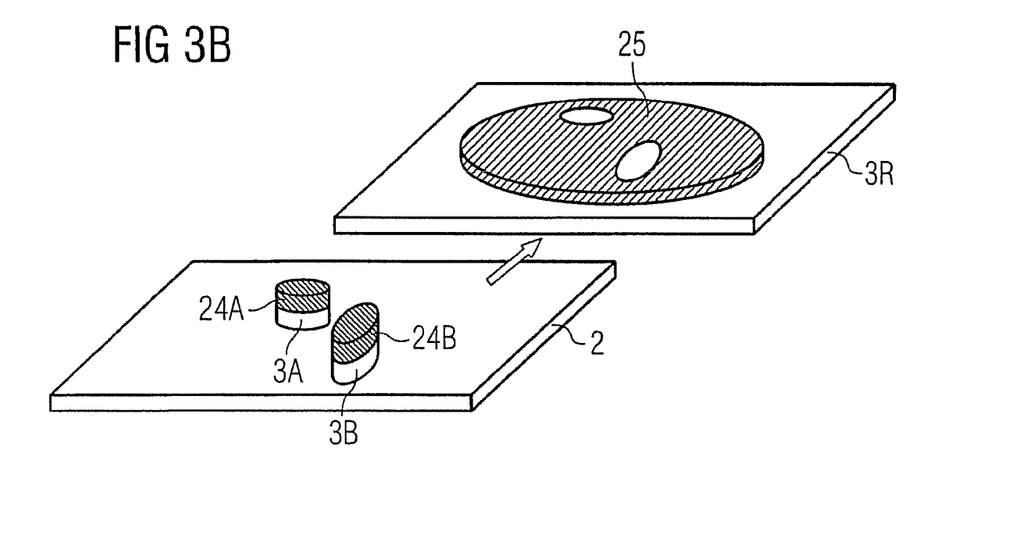

The case in which the target zone 14 itself is excised is represented in FIGS. 3A and 3B. In this case, the target zone comprises a plurality of mutually separated regions 24A and 24B, which are spatially surrounded by a preparation segment 25 not belonging to the target zone. In this case, the regions 24A and 24B of the preparation 4 are excised. As shown in FIG. 3B, after the non-excised segment 3R of the incisable membrane 3 is removed, the regions 24A and 24B of the target zone remain on the carrier 2 together with the corresponding excised segments 3A and 3B of the incisable membrane 3. The preparation segment 25 not contained in the target zone is removed together with the non-excised segment 3R of the incisable membrane 3. In the case represented in FIGS. 3A and 3B, the preparation is cut along the entire edge of the target zone 24A, 24B.

Whether it is expedient to excise the target zone itself or the preparation segments not contained in the target zone may be determined either by user input or automatically. In particular, the computer that defines the incision lines may determine, based upon the selected target zone, whether it is more advantageous to excise the target zone or the preparation segments not contained in the target zone. Criteria for this, as may be seen in FIGS. 2A, 2B, 3A, and 3B, are, for example, whether the target zone is a geometrically connected region, i.e., whether each point of the target zone can be reached from any other point of the target zone without having to leave the target zone, or whether the target zone occupies a proportion, which exceeds a predetermined threshold value, of the total area of the preparation.

As will now be presented by way of example with reference to FIGS. 4, 5A, 5B, and 5C, the target zone may be further processed or analyzed in a wide variety of ways after it has been separated and taken. For simpler presentation, these explanations will be restricted to the case in which the target zone itself is excised and, therefore, remains on the carrier 2 after the non-excised segment 3R of the incisable membrane 3 is removed.

The target zone remaining on the carrier 2 may be wetted directly with process chemicals, which may, for example, be applied with point-wise accuracy in the form of drops by a liquid handling system. To this end, the coordinates of the target zone, as determined in the microdissection method, may be provided to the liquid handling system.

The target zone may also be taken off manually or automatically from the carrier 2 using a sterile tool and, for example, subsequently introduced into a test tube of process chemicals.

Figure 4:
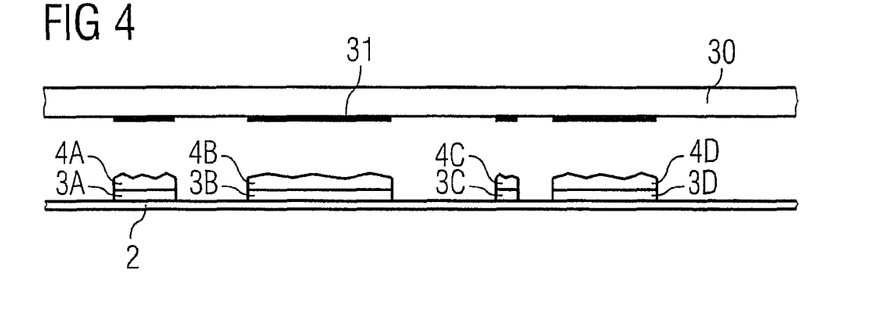
FIG. 4 is a fragmentary cross-sectional view of further processing of microdissectates obtained by a microdissection method according to an exemplary embodiment of the invention.

As shown in FIG. 4, an impression of the target zone may also be taken by pressing a carrier 30, coated with a process gel or a digestion gel, onto the carrier 2 with the target zone 4A-4D disposed thereon. The impression 31 may, for example, be used for matrix assisted laser desorption/ionization (MALDI) methods.

Figure 5A:
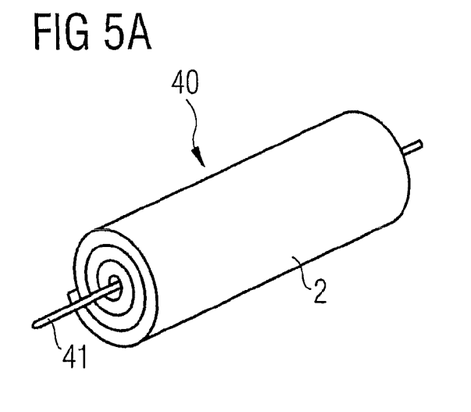
FIG. 5A is a perspective view of further processing of microdissectates obtained by another microdissection method according to an exemplary embodiment of the invention.
Figure 5B:
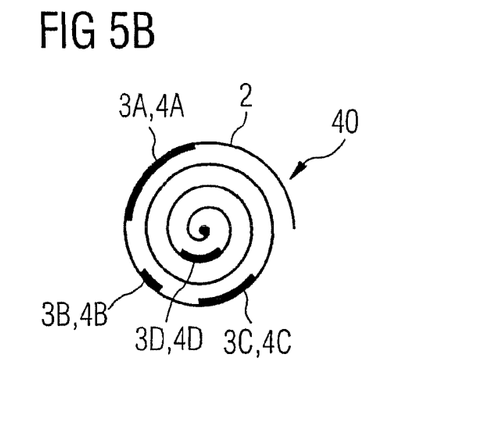
FIG. 5B is a plan view of further processing of microdissectates obtained by a microdissection method according to an exemplary embodiment of the invention.
Figure 5C:
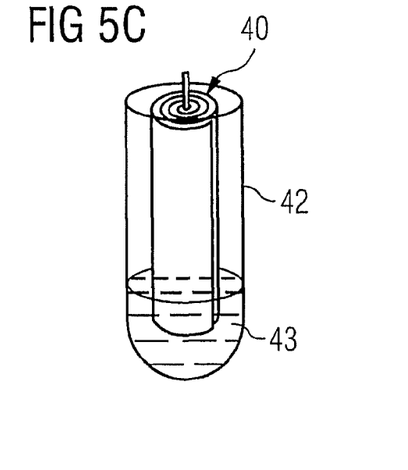
FIG. 5C is a perspective and partially transparent view of further processing of microdissectates obtained by a microdissection method according to an exemplary embodiment of the invention.

As represented in FIGS. 5A to 5C, the target zone may also be centrifuged off from the carrier 2. To this end, the carrier 2 is advantageously configured as a membrane, for example, made of polytetrafluoroethylene (PTFE), and the incisable membrane 3 is applied on the carrier 2 so that the excised segments 3A-3D of the incisable membrane 3 can be displaced laterally along the carrier 2. The carrier 2 is, then, rolled up together with the excised segments 3A-3D of the incisable membrane 3 and the excised segments 4A-4D of the preparation 4, i.e., the target zone of the preparation 4, to form a roll 40 as shown in FIGS. 5A and 5B. To facilitate the rolling, a pin 41 may be applied on an edge of the carrier 2.

As shown in FIG. 5C, the roll 40 is then put into a centrifuge tube 42 into which a process liquid 43 is introduced. Due to the centrifugal forces occurring during centrifuging, lateral forces act on the excised segments 3A-3D of the incisable membrane 3, which displace the segments 3A-3D towards the edge of the carrier 2 together with the excised segments of the preparation that are disposed thereon. The effect achieved by this is that all or most of the excised segments 4A-4C of the preparation 4 slide into the process chemical 43, where, for example, they are lysed. The carrier 2 is then taken away, and the lysis liquid is analyzed further. For a possible application in proteomics for example, the lysis liquid may be prepared, a proteinase-K digestion may be carried out and the resulting preparation may be provided to suitable study methods, for example, nanoliquid chromatography or mass spectroscopy.

Various exemplary embodiments of carrier devices, which may advantageously be used for the microdissection method according to embodiments of the invention, will now be discussed with reference to FIG. 6. As already explained with reference to FIGS. 1-3, the carrier device comprises an incisable membrane and a carrier. The carrier advantageously, in turn, comprises two supports, for example, two membranes or one membrane and one glass carrier, which are applied on one another by adhesion or by an adhesive or another medium introduced therebetween.

Figure 6A:
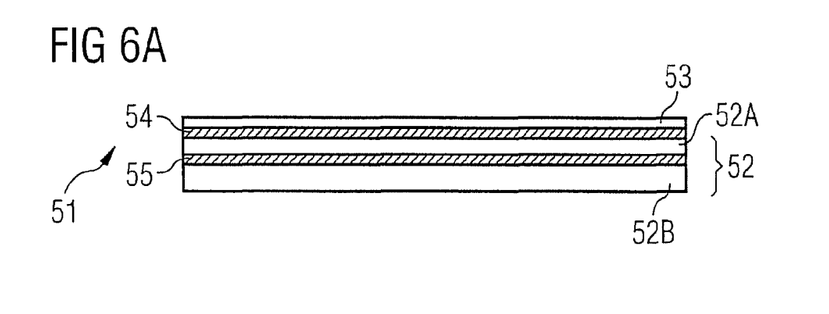
FIGS. 6A, 6B, and 6C are fragmentary, cross-sectional views of various exemplary embodiments of a carrier device according to the invention.

FIG. 6A shows an exemplary embodiment of the carrier device 51 according to one embodiment of the invention with an incisable membrane 53 and a carrier 52, which comprises a first PTFE membrane 52A and a second PTFE membrane 52B. The membranes are joined together by a glycerol layer 55 introduced between them. A glycerol layer 54 is likewise introduced between the incisable membrane 53 and the first PTFE membrane 52A. The glycerol layer 54 serves several purposes. In particular, it may facilitate removal of the incisable membrane 53 from the first membrane 52A and, furthermore, helps the excised segments of the incisable membrane 53 to remain adhering on the first membrane 52A when the non-excised segment of the incisable membrane 53 is removed. When centrifuging off the target zone, as explained above with reference to FIG. 5, the glycerol layer 54 improves the lateral displaceability of the excised segments of the incisable membrane 53 relative to the first membrane 52A.

Figure 6B:
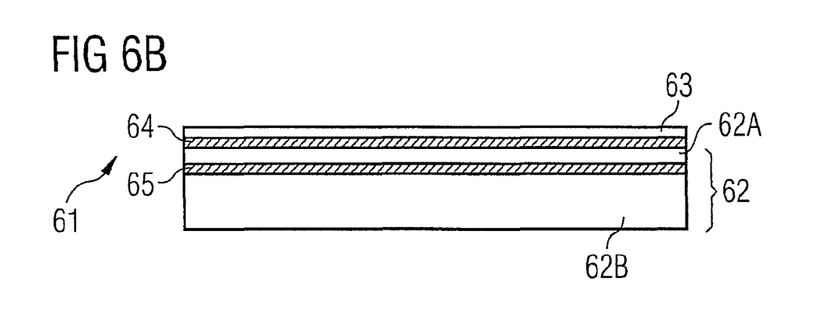

FIG. 6B shows another exemplary embodiment of a carrier device 61 according to one embodiment of the invention with an incisable membrane 63 and a carrier 62, which comprises a PTFE membrane 62A and a glass carrier 62B, between which a glycerol layer 65 is, in turn, introduced.

The configurations for a carrier device as represented in FIGS. 6A and 6B, which comprises in total at least three material layers, for example, three membranes or two membranes and one glass carrier, is advantageous in particular when the target zone is excised and remains on the carrier as explained with the aid of FIG. 3. In this case, the configuration of the carrier device as represented in FIGS. 6A and 6B makes it possible for the membrane 52A or 62A, respectively, to be removed from the second membrane 52B or the glass carrier 62B, and for the target zone disposed on the membrane 52A or 62A to be made available for further processing or analysis on the removed membrane 52A or 62A.

Figure 6C:
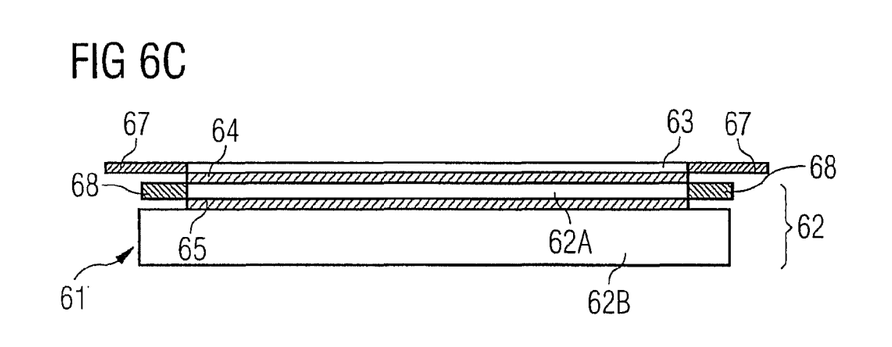

FIG. 6C shows a variant of the carrier device shown in FIG. 6B. Laterally protruding appendages or tabs 67 and 68 are provided both on the incisable membrane 63 and on the membrane 62A. The tabs do not adhere to the neighboring layers of the carrier device and they, thus, facilitate manual removal of the incisable membrane 63 from the membrane 62A, or the membrane 62A from the glass plate 62B, respectively. Naturally, the tabs 67, 68 could also be provided similarly in the exemplary embodiment of the carrier device as shown in FIG. 6A.

Figure 7A:
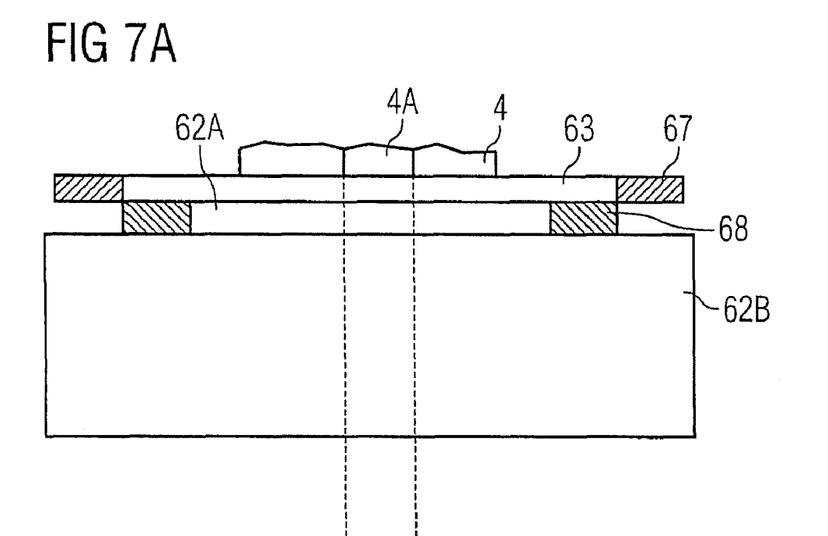
FIGS. 7A and 7B are fragmentary, cross-sectional views illustrating use of a carrier device according to an exemplary embodiment of the invention in a microdissection method according to an exemplary embodiment of the invention.
Figure 7B:
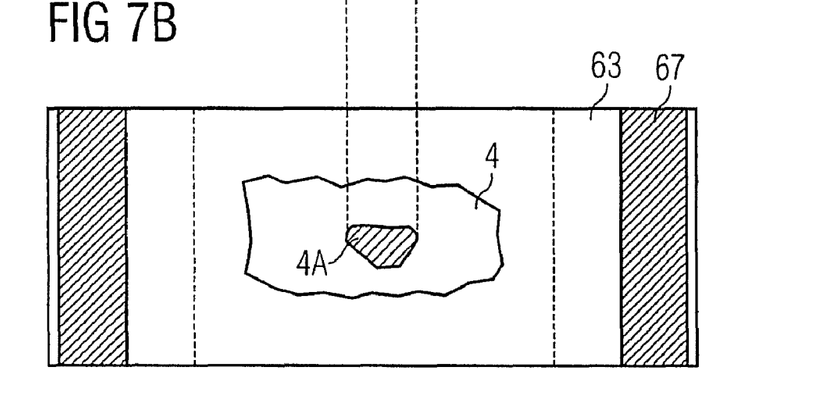

FIG. 7 schematically represents the use of the carrier device of FIG. 6C in the microdissection method according to one embodiment of the invention, FIG. 7A being a cross-sectional view and FIG. 7B being a plan view. After the segment 4A of the preparation has been excised, the incisable membrane 63 can easily be gripped on one of the tabs 67 and removed from the carrier.

Carrier devices according to embodiments of the invention, such as are represented in FIG. 6, may however be used not only in the microdissection method according to embodiments of the invention. Rather, they may also be used in microdissection methods in which excised segments or objects of the preparation are transported to a collection device by laser irradiation, as described, for example, in International Publication Nos. WO 97/29355 A or WO 01/73398 A in the name of the Applicant. Also, when used in this way, carrier devices with a three-layer structure, as is shown in FIG. 6, allow segments of the preparation that remain on the carrier to be delivered simply for further processing.

The invention claimed is:

1. A method for performing microdissection, which comprises:
providing a carrier device with a laser light-absorbent incisable layer and a carrier for carrying the laser light-absorbent incisable layer;
applying a preparation on the incisable layer;
selecting a target zone to be separated from the preparation;
cutting the preparation and the incisable layer along an edge segment of the target zone by laser irradiation to subdivide the incisable layer into at least one excised segment and a non-excised segment; and
removing the non-excised segment of the incisable layer from the carrier.

2. The method according to claim 1, which further comprises:
carrying out the cutting step to excise the target zone; and
removing the non-excised segment of the incisable layer while the target zone remains on the carrier.

3. The method according to claim 2, which further comprises:
applying the incisable layer displaceably on the carrier; and
centrifuging off the target zone together with the at least one excised segment of the incisable layer from the carrier for further processing of the target zone.

4. The method according to claim 1, which further comprises:
carrying out the cutting step to excise a preparation segment not containing the target zone; and
removing the target zone from the carrier together with the non-excised segment of the incisable layer when the non-excised segment is removed.

5. The method according to claim 1, which further comprises carrying out the removing step manually.

6. The method according to claim 1, wherein the carrier comprises a first incisable layer support and a second support operable to support the first support; and which further comprises configuring the carrier device to dispose the first support substantially between the second support and the incisable layer.

7. The method according to claim 6, which further comprises removing the first support from the second support after the non-excised segment of the incisable layer is removed from the carrier.

8. The method according to claim 7, which further comprises manually removing the first support from the second support.

9. The method according to claim 1, which further comprises
generating an overview image of the preparation;
carrying out the target zone selecting step one of in a user-defined fashion and at least partially automatically based upon the overview image.

10. The method according to claim 1, wherein the carrier is at least partially transparent; and which further comprises irradiating a laser beam onto the carrier device on the same side as the carrier to cut the preparation and the incisable layer.

11. The method according to claim 1, which further comprises irradiating a laser beam onto the carrier device on the same side as the incisable layer to cut the preparation and the incisable layer.

12. The method according to claim 1, wherein the target zone is a plurality of respectively geometrically connected target zone regions having edge segments, and which further comprises cutting the preparation and the incisable layer by laser irradiation along an edge segment of each of the target zone regions before the non-excised segment of the incisable layer is removed.

13. The method according to claim 1, which further comprises analyzing the target zone by molecular genetics after the non-excised segment of the incisable layer is removed from the carrier.

14. The method according to claim 1, wherein the preparation is a biological preparation.

15. A method for performing microdissection, comprising:
providing a carrier device with a laser light-absorbent incisable layer and a means for carrying the laser light-absorbent incisable layer;
applying a biological preparation on the incisable layer;
selecting a target zone to be separated from the preparation;
cutting the preparation and the incisable layer along an edge segment of the target zone by laser irradiation to subdivide the incisable layer into at least one excised segment and into a non-excised segment; and
removing the non-excised segment of the incisable layer from the carrier means.

* * * * *